United States Patent
Huang et al.

(10) Patent No.: US 9,579,016 B2
(45) Date of Patent: Feb. 28, 2017

(54) NON-INVASIVE 3D IMAGING AND MEASURING OF ANTERIOR CHAMBER ANGLE OF THE EYE

(71) Applicants: OREGON HEALTH & SCIENCE UNIVERSITY, Portland, OR (US); ZHEJIANG UNIVERSITY, Zhejiang (CN)

(72) Inventors: David Huang, Portland, OR (US); Yan Li, Portland, OR (US); Wei Wu, Zhejiang (CN); Huilong Duan, Hangzhou (CN)

(73) Assignee: Oregon Health & Science University, Portland, OR (US)

( * ) Notice: Subject to any disclaimer, the term of this patent is extended or adjusted under 35 U.S.C. 154(b) by 129 days.

(21) Appl. No.: 14/407,668

(22) PCT Filed: Jun. 17, 2013

(86) PCT No.: PCT/US2013/046190
§ 371 (c)(1),
(2) Date: Dec. 12, 2014

(87) PCT Pub. No.: WO2013/188885
PCT Pub. Date: Dec. 19, 2013

(65) Prior Publication Data
US 2015/0150447 A1 Jun. 4, 2015

Related U.S. Application Data

(60) Provisional application No. 61/660,670, filed on Jun. 15, 2012.

(51) Int. Cl.
*A61B 3/12* (2006.01)
*A61B 3/10* (2006.01)
(Continued)

(52) U.S. Cl.
CPC ............. *A61B 3/102* (2013.01); *A61B 3/117* (2013.01); *G06T 7/0014* (2013.01);
(Continued)

(58) Field of Classification Search
CPC ........... A61B 3/102; A61B 3/14; A61B 6/032; A61B 8/483; A61B 1/05; A61B 3/12; A61B 5/0064
(Continued)

(56) References Cited

U.S. PATENT DOCUMENTS

2007/0216909 A1  9/2007  Everett et al.
2008/0074617 A1  3/2008  Podoleanu
(Continued)

OTHER PUBLICATIONS

Memarzadeh, Farnaz et al., "Interpretation of Angle Images," Imaging the Eye from Front to Back with RTVue Fourier-Domain Optical Coherence Tomography, Slack, Incorporated, Thorofare, NJ, 2010, pp. 47-52.
(Continued)

*Primary Examiner* — Hung Dang
(74) *Attorney, Agent, or Firm* — Schwabe, Williamson & Wyatt, P.C.

(57) ABSTRACT

Embodiments of OCT measurement and analysis techniques described herein enable precise 3D anterior chamber angle measurement from major, pertinent landmarks in the eye. Such techniques result in a more reliable, quantifiable angle measurement technique that is both non-invasive and non-contact in nature, thereby improving clinical practicality, while improving patient comfort and care. For example, a method is provided for in vivo imaging of an eye, including taking a plurality of optical coherence tomography (OCT) line scans of an eye to obtain a 3-dimensional (3D) radial scan pattern, the individual line scans including a plurality of axial scans, and obtaining a three-dimensional image of an anterior chamber angle of the eye from the radial scan pattern.

36 Claims, 15 Drawing Sheets

(51) Int. Cl.
*A61B 3/117* (2006.01)
*G06T 7/00* (2006.01)
*G01B 9/02* (2006.01)

(52) U.S. Cl.
CPC ..... *G01B 9/02091* (2013.01); *G06T 2207/10101* (2013.01); *G06T 2207/30041* (2013.01)

(58) Field of Classification Search
USPC .......................... 351/206, 246, 209, 210, 221
See application file for complete search history.

(56) References Cited

U.S. PATENT DOCUMENTS

| | | |
|---|---|---|
| 2008/0309881 A1 | 12/2008 | Huang et al. |
| 2011/0081000 A1 | 4/2011 | Gertner et al. |
| 2012/0140174 A1 | 6/2012 | Hee et al. |
| 2014/0307226 A1* | 10/2014 | Lathrop ............... A61B 3/0025 351/206 |

OTHER PUBLICATIONS

Cheung, Carol Y., et al., "Novel Anterior-chamber Angle Measurements by High-definition Optical Coherence Tomography Using the Schwalbe Line as the Landmark," Br J. Ophthalmol, 2011, vol. 95, No. 7, pp. 955-959.

Ishikawa H. et al., "Quantitative Assessment of the Anterior Segment Using Ultrasound Biomicroscopy," Currrent Opinion in Opthalmology, Apr. 2000, vol. 11, No. 2, pp. 133-139.

Tian, Jing et al., "Automatic Anterior Chamber Angle Assessment for HD-OCT Images," IEEE Transactions on Biomedical Engineering, Nov. 2011, vol. 58, No. 11, pp. 3242-3249.

Radhakrishnan, Sunita et al., "Comparison of Optical Coherence Tomography and Ultrasound Biomicroscopy for Detection of Narrow Anterior Chamber Angles," Arch Opthalmol, Aug. 2005, vol. 123, No. 8, pp. 1053-1059.

* cited by examiner

NON-INVASIVE 3D IMAGING AND MEASURING OF ANTERIOR CHAMBER ANGLE OF THE EYE

CROSS REFERENCE TO RELATED APPLICATIONS

The present application claims priority to U.S. Provisional Patent Application No. 61/660,670, filed on Jun. 15, 2012, and titled "NON-INVASIVE 3-D IMAGING AND MEASURING OF ANTERIOR CHAMBER ANGLE OF THE EYE," the entire disclosure of which is hereby incorporated by reference.

ACKNOWLEDGMENT OF GOVERNMENT SUPPORT

This invention was made with government support under grant numbers R01-EY018184 awarded by the National Institutes of Health. The government has certain rights in the technology.

FIELD

This disclosure relates generally to the field of biomedical imaging, and more specifically to methods, apparatuses, and systems associated with optical coherence tomography.

BACKGROUND

Glaucoma is the second leading cause for blindness worldwide. Primary angle-closure glaucoma is one of the most common sub-types of glaucoma. Evaluating the anterior chamber angle of the eye is an important component in glaucoma diagnosis and management. Gonioscopy remains the clinical standard for assessing the anterior chamber angle in the eye. However, gonioscopy is a subjective method and can be easily affected by factors including patient cooperation, examiner skill, and the type of lens used. Moreover, gonioscopy does not provide quantitative evaluation of the anterior chamber angle.

Ultrasound biomicroscopy (UBM) is another method for providing high-resolution images of the anterior chamber angle. The disadvantages of UBM include invasive contact with the eye using a coupling medium, anesthesia, need for a skilled examiner, and long image acquisition time. Additionally, Scheimpflug imaging devices, such as Pentacam (Oculus, Lynnwood, Wash., USA) or Galilei (Ziemer Ophthalmic Systems AG, Switzerland), are non-contact instruments that provide another method for imaging the anterior segment of the eye. However, Scheimpflug imaging does not provide sufficient information of the anterior chamber angle due to light scattering and limited image resolution. Therefore, methods for non-invasive imaging of the anterior chamber angle of the eye that provide quantitative detail and measurement are of substantial clinical importance.

Optical coherence tomography (OCT) is a non-contact imaging modality for high-resolution, depth-resolved cross-sectional, and 3-dimensional (3D) imaging of biological tissue. Among its many applications, ocular imaging in particular has found widespread clinical use. OCT imaging can be performed quickly and easily with minimal expertise. It can provide cross-sectional images of the anterior chamber angle with micron level resolution. These advantages make OCT suitable for both qualitative and quantitative angle evaluation. Several parameters, such as angle opening distance (AOD), trabecular-iris space area (TISA), and angle recess area (ARA), have been developed to provide quantitative assessment of the anterior chamber angle. These parameters had been proven to have excellent correlation with gonioscopy in terms of the identification of occludable angles.

Traditional OCT technique commonly acquires 2-dimensional (2D) images of one angle location at a time. Alternatively, the OCT image may contain two opposite angles (such as temporal and nasal), if wide-scan anterior segment images are acquired. Anterior chamber angle configuration may vary quickly even inside the same angle quadrant. Therefore, the 2D-OCT technique has its limitations and cannot provide complete information of the entire angle quadrant. OCT scan patterns to image the anterior chamber angle 3-dimensionally (3D) and methods that provide for qualitative and quantitative 3D angle assessment would enable OCT to become a clinically important non-invasive glaucoma diagnosis and management technique for 3D imaging and measuring of the anterior chamber angle of the eye.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF DISCLOSED EMBODIMENTS

Figure 1:
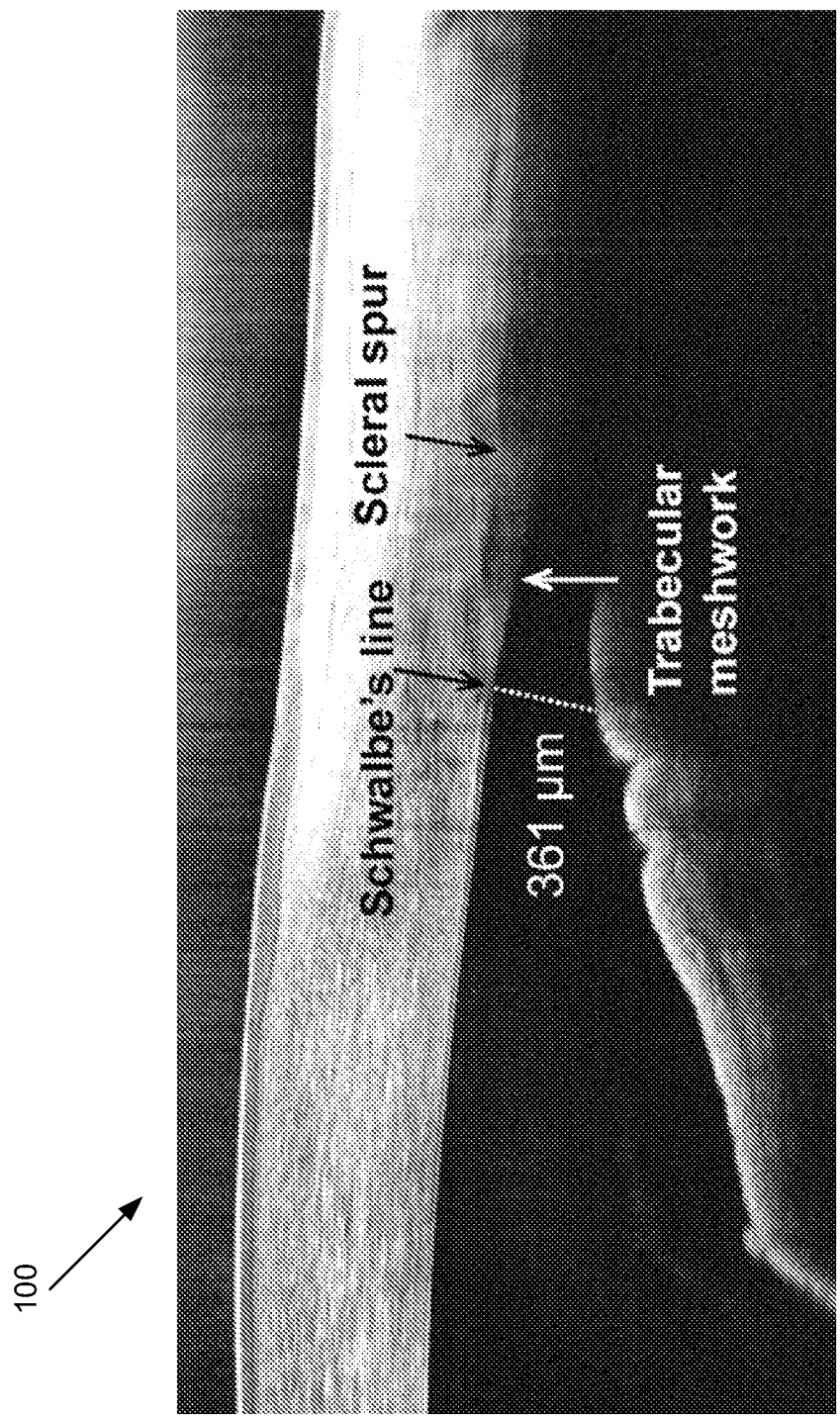
FIG. 1 illustrates in vivo cross-sectional OCT images of the anterior chamber angle with micron level resolution.

In the following detailed description, reference is made to the accompanying drawings which form a part hereof and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

A phrase in the form of "NB" means "A or B." A phrase in the form "A and/or B" means "(A), (B), or (A and B)." A phrase in the form "at least one of A, B and C" means "(A), (B), (C), (A and B), (A and C), (B and C) or (A, B and C)." A phrase in the form "(A) B" means "(B) or (A B)," that is, A is optional.

In various embodiments of the present invention, methods, apparatuses, and systems for biomedical imaging are provided. In exemplary embodiments herein, one or more computing devices may be endowed with one or more components of the disclosed articles of manufacture and/or systems and may be employed to perform one or more methods as disclosed herein.

In various embodiments, structure information of a sample may be obtained using optical coherence tomography (OCT) imaging based on the detection of spectral interference. Such imaging may be two-dimensional (2-D) or three-dimensional (3-D), depending on the application. Structural imaging may be of an extended depth range relative to prior art methods. Imaging and related aspects of the methods herein may be performed by an OCT imaging device coupled to, or integrated with, one or more computing devices.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

Embodiments herein provide methods, apparatuses, and systems for 3D imaging and measuring of the anterior chamber angle of the eye utilizing optical coherence tomography (OCT). In embodiments, a radial scan pattern of the eye may be acquired that includes a plurality of radial line scans oriented in line with a common center point and oriented at an angle from one another. The radial line scans may each include a plurality of axial scans. In some embodiments, the radial scan pattern may be acquired by directly taking a plurality of radial line scans using an OCT system. Alternatively, or additionally, the radial scan pattern may be acquired by taking a plurality of parallel line scans of a volumetric scan, and resampling the volumetric scan to obtain the radial scan pattern.

In various embodiments, the radial scan pattern may cover an angular region of the eye (e.g., a range of angles from the common center point). In some embodiments, the angular region may be less than 360 degrees, and the radial scan pattern may form a fan-shaped scan pattern. In some embodiments, a plurality of fan-shaped scan patterns may be acquired at different rotational positions around the eye. In other embodiments, the radial scan pattern may cover a 360 degree region of the eye around the common center point. Such a radial scan pattern may form a cylindrical or annular scan pattern.

In various embodiments, the radial scan pattern may be used for qualitative and quantitative imaging of the eye. In some embodiments, the radial line scans at one or more key frame locations of the radial scan pattern may be averaged, and a location of an anatomical landmark of the eye (e.g., Schwalbe's line) may be identified at the one or more key frame locations. The location of the anatomical landmark may then be identified in intermediate frame locations of the radial scan based on the locations of the anatomical landmark identified in the key frame locations.

In some embodiments, a synthetic B-scan may be formed from the radial scan pattern that includes a column of pixels from each frame (e.g., radial line scan) of the 3D scan pattern. The columns of pixels may have a common orientation with respect to an anatomical landmark of the eye. For example, the columns of pixels may be perpendicular to a posterior corneal surface of the eye. In some embodiments, the angle opening distance of the eye may be measured from the synthetic B-scan.

In some embodiments, the radial scan pattern may be used to determine an area or volume of a region of the eye. For example, an area of a region (e.g., defined by one or more anatomical landmarks) may be measured in the plurality of radial line scans. A volume of the region may then be calculated based on the measured areas. The region may include, for example, an angle recess and/or trabecular-iris space of the eye.

In some embodiments, Schlemm's canal area may be measured in the plurality of line scans. The measured Schlemm's canal areas may be averaged to obtain an average Schlemm's canal area.

In various embodiments, one or more non-transitory computer-readable media are provided, the one or more computer-readable media having instructions, stored thereon, that, when executed, cause a computing system to perform one or more methods as described herein.

Illustrated in FIG. 1 is in vivo cross-sectional 840 nm OCT image 100 of the anterior chamber angle with micron level resolution. One of the anatomical landmarks used for AOD measurements, Schwalbe's line, is reflected here for reference and general overview. The angle opening distance at Schwalbe's line (AOD-SL, marked by a white dotted line) was measured to be 361 µm in this example.

3D Anterior Chamber Angle Scan Pattern

Figure 2:
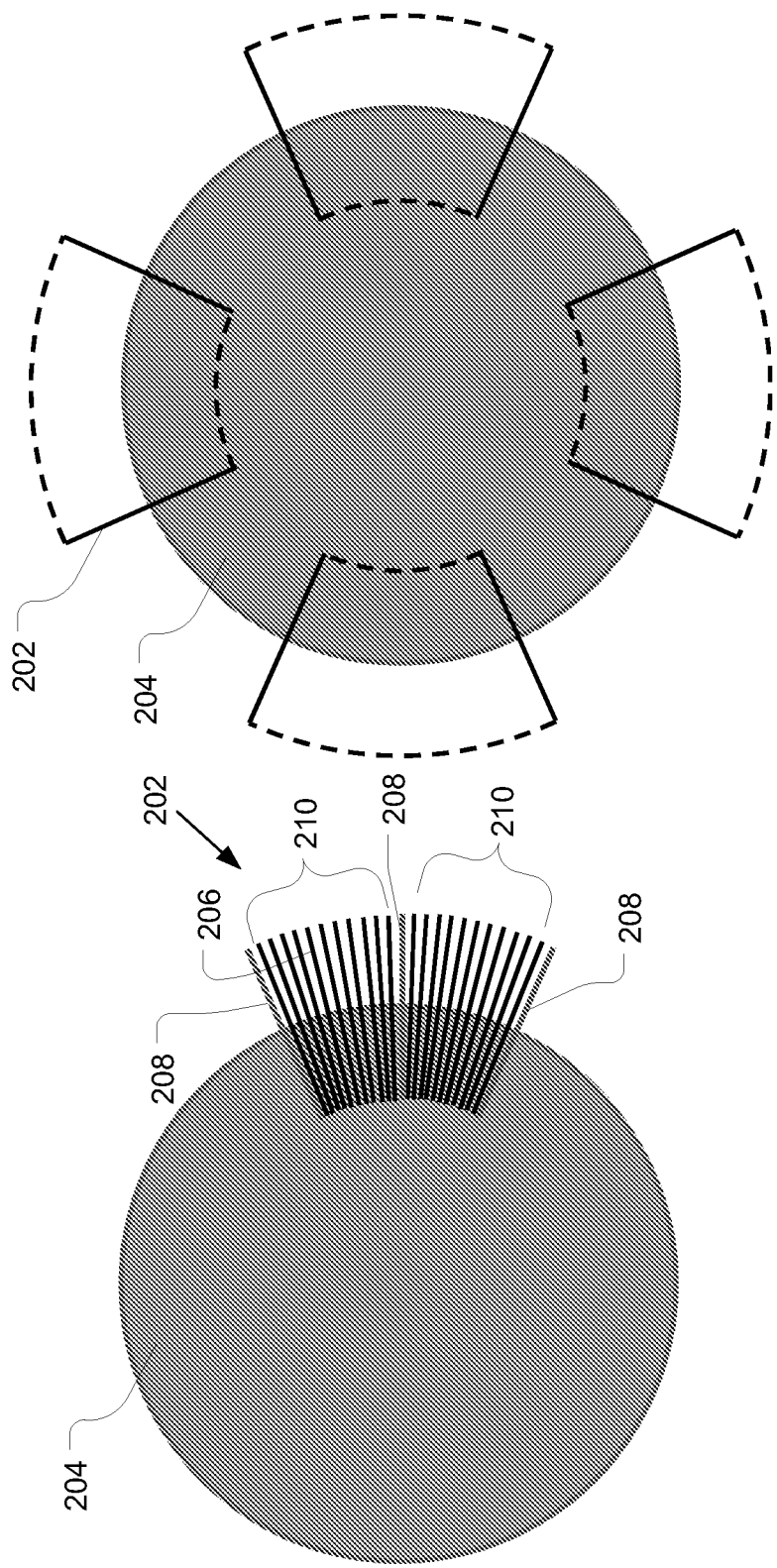
FIG. 2A schematically illustrates a 3D radial scan pattern of an eye in accordance with various embodiments.
FIG. 2B schematically illustrates a plurality of 3D radial scan patterns rotated about the eye to acquire 3D angle images of different angle quadrants.

FIG. 2A illustrates a 3D radial scan pattern 202 of eye 204 in accordance with various embodiments. Radial scan pattern 202 is a fan-shaped scan pattern with a plurality of OCT radial line scans 206 arranged at an angle from one another. Each radial line scan 206 may include a plurality of axial scans (e.g., in a direction perpendicular to the line of radial line scans 206 shown in FIG. 2A). Thus, the scan pattern 202 may be a 3D scan pattern.

In some embodiments, the radial line scans 206 may be oriented toward a common center point (e.g., at the center of the eye 204). The radial line scans 206 may have any suitable length, and adjacent line scans 206 may be oriented at any suitable angle from one another. For example, the radial line scans 206 may have a length of about 3 to about 10 millimeters (mm), and adjacent radial line scans 206 may be oriented at an angle of about 0.5-5 degrees, such as 2 degrees, apart. The scan pattern 202 may include any suitable number of radial line scans 206. For example, the scan pattern 202 shown in FIG. 2A includes radial line scans 206 at 25 frame locations to cover a 48 degree area (±24° from a center angle of the scan pattern 202). In some embodiments, the scan pattern 206 may be straddled on the limbus area assuming 12-mm corneal diameter.

The scan pattern 202 may include a plurality of radial line scans at one or more key frame locations 208. For example, the key frame locations 208 may be at the center angle (0 degrees), and at angles evenly spaced on either side of the center angle (e.g., +24 degrees and −24 degrees, as shown in FIG. 2A). Any suitable number of radial line scans 206 may be taken at the key frame locations 208. In one example, eight repeated line scans 206 may be acquired at the key frame locations 208. The plurality of line scans 206 at the key frame locations 208 may be used, for example, for frame averaging (e.g., averaging the results of the plurality of line scans 206 from the same frame location).

In various embodiments, a lower number of line scans 206 may be acquired at intermediate frame locations 210 of the scan pattern 202 (e.g., the frame locations other than the key frame locations 208). For example, in some embodiments, a single line scan 206 may be taken at non-key frame locations 210.

In one example, a scan pattern 202 with eight repeated scans at three key frame locations 208, and twenty-two intermediate line scans at respective intermediate frame locations 210, can be acquired in 0.9 second, assuming each line scan 206 has a length of 4 mm and includes 512 axial scans and an OCT system with a scan speed of 26,000 axial scan per second is used.

As shown in FIG. 2B, in some embodiments, a plurality of 3D scan patterns 202 may be acquired at different locations of the eye 204. For example, the plurality of 3D scan patterns 202 may be rotated with respect to one another.

The 3D angle scan pattern 202 shown in FIGS. 2A and 2B can be used to demonstrate the quantitative 3D angle measurements described herein. However, alternative scan patterns with a different size, scan density, scan configuration, key frame location(s), and/or repetition number can also be used.

Figure 3:
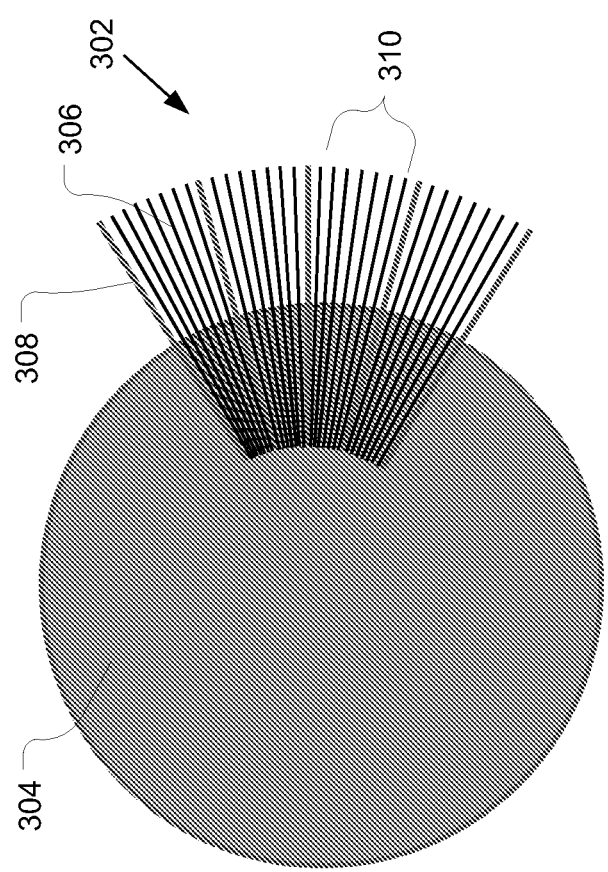
FIG. 3 schematically illustrates another 3D radial scan pattern in accordance with various embodiments.

For example, FIG. 3 illustrates an alternative 3D scan pattern 302 in accordance with various embodiments. Scan pattern 302 includes a fan-shaped scan pattern with 6-mm long radial line scans 306 arranged 2 degrees apart to cover a 64 degree area of eye 304 (e.g., ±32 degrees with respect to a center angle). A plurality of radial line scans 306 may be acquired at five key frame locations 308 (e.g., 0°, ±16°, ±32°).

Figure 4B:
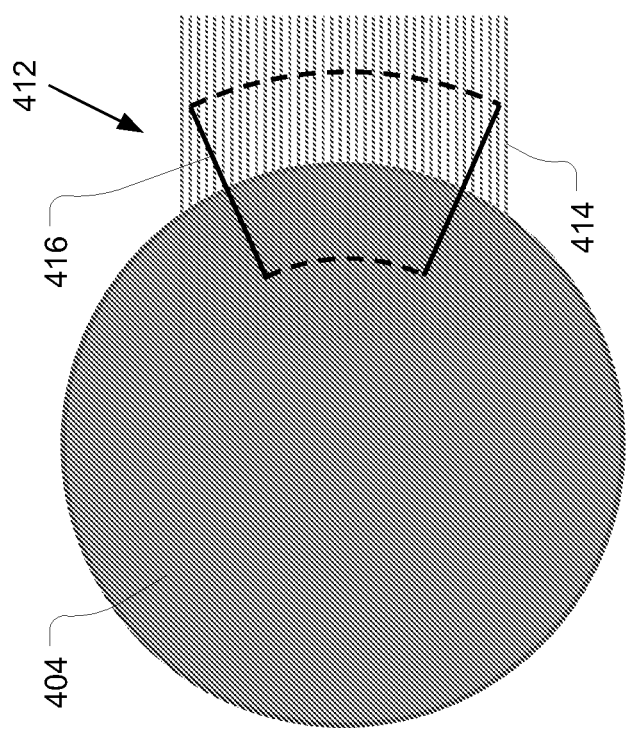
FIG. 4B schematically illustrates how a volumetric scan is resampled to form a radial scan pattern for quantitative 3D angle measurements.
Figure 4A:
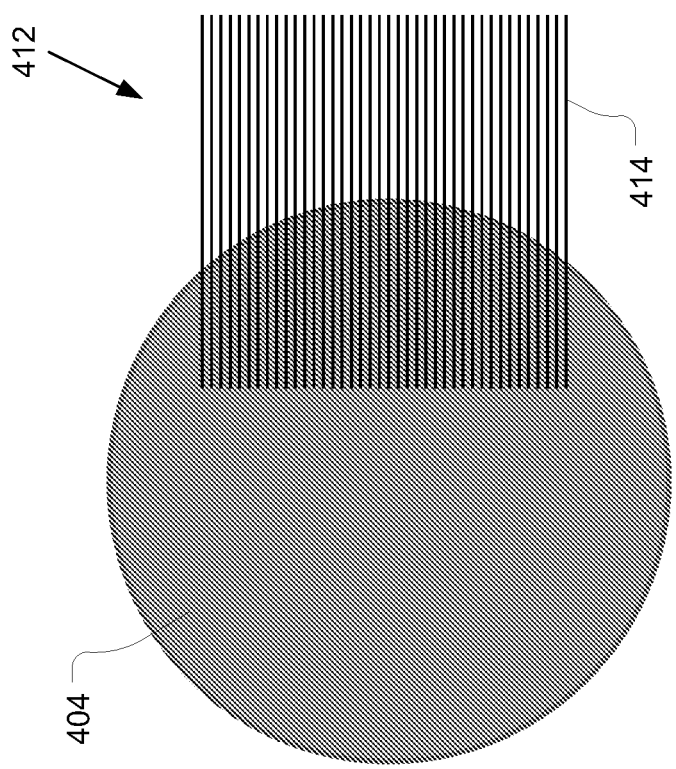
FIG. 4A schematically illustrates a 3D volumetric scan with a plurality of parallel line scans in accordance with various embodiments.

FIGS. 4A and 4B illustrate another alternative implementation for imaging of an eye 404 in accordance with various embodiments. As shown in FIG. 4A, a rectangular volumetric scan 412 may be acquired in a region of the eye 404. The volumetric scan 412 may include a plurality of parallel line scans 414. The line scans 414 may each include a plurality of axial scans. In some embodiments, the volumetric scan may have a higher density of line scans 414 and/or axial scans than the radial scan pattern 202 or 302. With a very high scan speed, dense and even volumetric scans 412 (such as a volumetric scan including 1024 raster scans with 1024 axial scan in each line scan, and a 6×6 mm scan area) may be acquired in a relatively short time period. In some embodiments, multiple volumetric scans 412 may be obtained for scan registration and averaging.

In various embodiments, the volumetric scan 412 may be resampled to obtain a radial scan pattern 416 (as shown in FIG. 4B) for quantitative 3D angle measurements. That is, some or all of the axial scans of the line scans 414 may be assigned to virtual radial line scans of the radial scan pattern 416.

3D Angle Opening Distance (AOD) Measurements

As noted above with FIG. 1, the anatomical landmark used for AOD measurements may be Schwalbe's line. The angle opening distance at Schwalbe's line (AOD-SL) may be measured as the length of line drawn perpendicular from Schwalbe's line on the posterior corneal surface to the anterior iris surface. In other embodiments, the AOD may be measured based on one or more other anatomical landmarks (including a location defined by one or more anatomical landmarks), for example as the perpendicular distance between the anatomical landmark and the anterior iris surface.

Figure 5A:
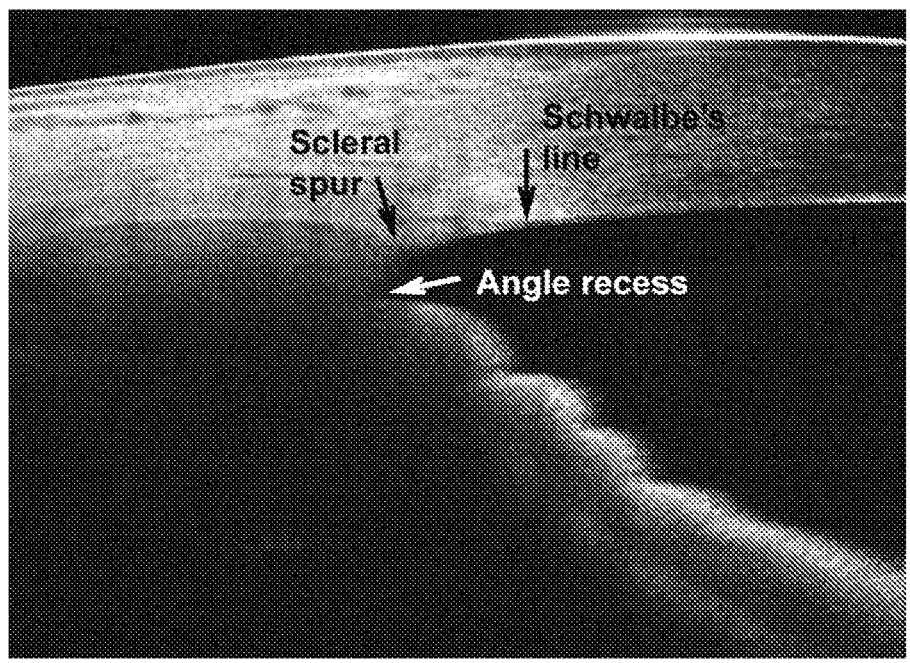
FIGS. 5A and 5B illustrates in vivo cross-sectional OCT images working at 1050 nm wavelength noting possible anatomical landmarks that may be used for 3D angle evaluation utilizing the techniques described herein.
Figure 5B:
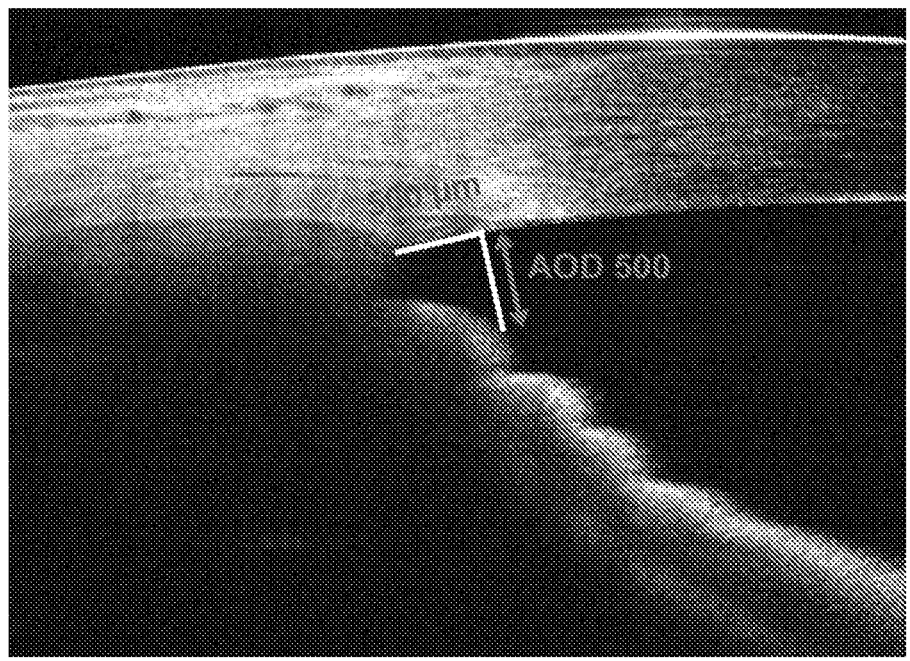

Other imaging systems, such as ultrasound biomicroscopy or OCT systems working at 1050 nm or 1310 nm wavelengths, may provide sufficient visualization on other anatomical landmarks, such as scleral spur and angle recess (see FIG. 5A). AOD measurements based on other anatomical landmarks, such as AOD-SS 500 µm (see FIG. 5B) or 750 µm anterior to the scleral spur (AOD-SS 500 or AOD-SS 750) can also be used for 3D angle evaluation with small changes to the techniques described herein.

Figure 6:
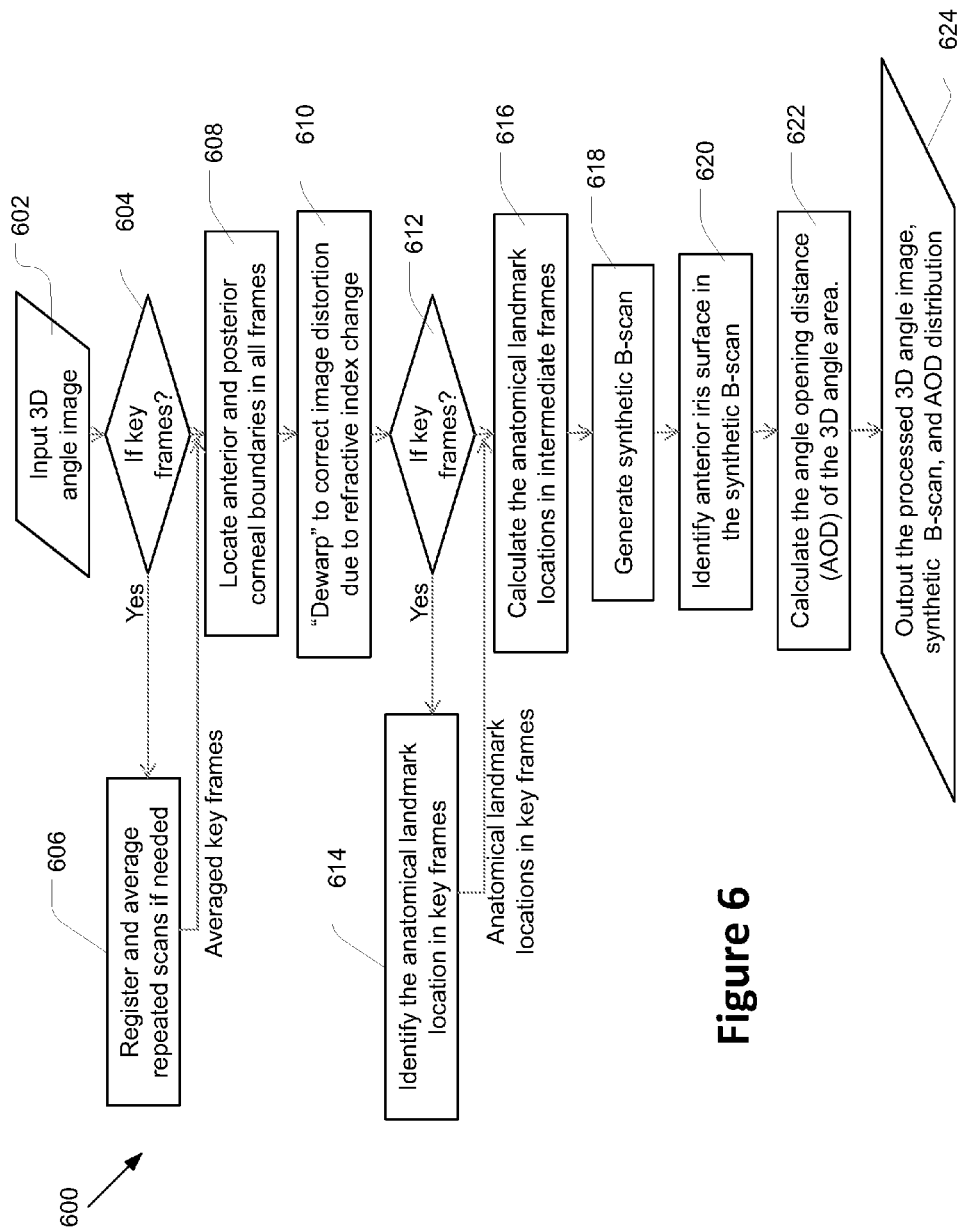
FIG. 6 is a flowchart showing a method for quantitative 3D angle opening distance (AOD) measurement in accordance with various embodiments.

FIG. 6 is a flowchart illustrating a method 600 for determining quantitative 3D AOD measurements in accordance with various embodiments. Method 600 is further described below. In some embodiments, one or more computer-readable media may be provided that have instructions, stored thereon, that, when executed, cause a computing system to perform one or more operations of the method 600.

Pre-Processing of the 3D Angle Images

At block 602, method 600 includes receiving a 3D angle image as an input. The 3D angle image may be for example, 3D scan pattern 202, 302, and/or 416, as described above. At blocks 604 and 606 of method 600, the repeated line scans acquired at the key frame locations may be registered and averaged. Frame averaging may increase the signal-to-noise ratio of the OCT scan and facilitate the detection of Schwalbe's line.

Next, at block 608, the anterior and posterior corneal surfaces may be detected using methods previously described in the art. For example, the anterior and posterior corneal surfaces may be detected using the methods described in Li Y, Shekhar R, Huang D, "Corneal pachymetry mapping with high-speed optical coherence tomography. Ophthalmology," 2006; 113(5):792-9 e2; Radhakrishnan S, See J, Smith S D, et al, "Reproducibility of anterior chamber angle measurements obtained with anterior segment optical coherence tomography," Invest Ophthalmol Vis Sci 2007; 48(8):3683-8; and/or Tian J, Marziliano P, Baskaran M, et al., "Automatic anterior chamber angle assessment for HD-OCT images," IEEE Trans Biomed Eng 2011; 58(11):3242-9; each of which are hereby incorporated by reference. In some embodiments, a computerized method may be used to identify the corneal boundaries by locating the maximum signal intensity and biggest gradient magnitude of OCT axial scans. Alternatively, or additionally, binary angle images may be calculated by thresholding the OCT image. Then the anatomical boundaries may be located with morphological operations.

At block 610 of method 600, image distortion due to refraction and transition of the group index at interfaces may be removed using a "dewarping" method (e.g., the dewarping method described in Westphal V, Rollins A M, Radhakrishnan S, Izatt J A, "Correction of geometric and refractive image distortions in optical coherence tomography applying Fermat's principle," Optics Express 2002; 10(9):397-404, which is hereby incorporated by reference).

At blocks 612 and 614 of method 600, an anatomical landmark, e.g., Schwalbe's line, may be identified from the key frames (e.g., 1st, 13th, and 25th frames). The anatomical landmark may be identified by either user manual input or computerized methods as previously described in the art. For example, Schwalbe's line may be located via a computerized method by locating the geometric shape change of the corneal endothelial boundary as demonstrated in above mentioned reference. Additional information regarding computerized methods for locating the anatomical landmark are described in Tian J, Marziliano P, Baskaran M, et al., "Automatic anterior chamber angle assessment for HD-OCT images," IEEE Trans Biomed Eng 2011; 58(11):3242-9, which is hereby incorporated by reference.

Locate the Anatomical Landmark in Key Frames and Intermediate Frames

Figure 7:
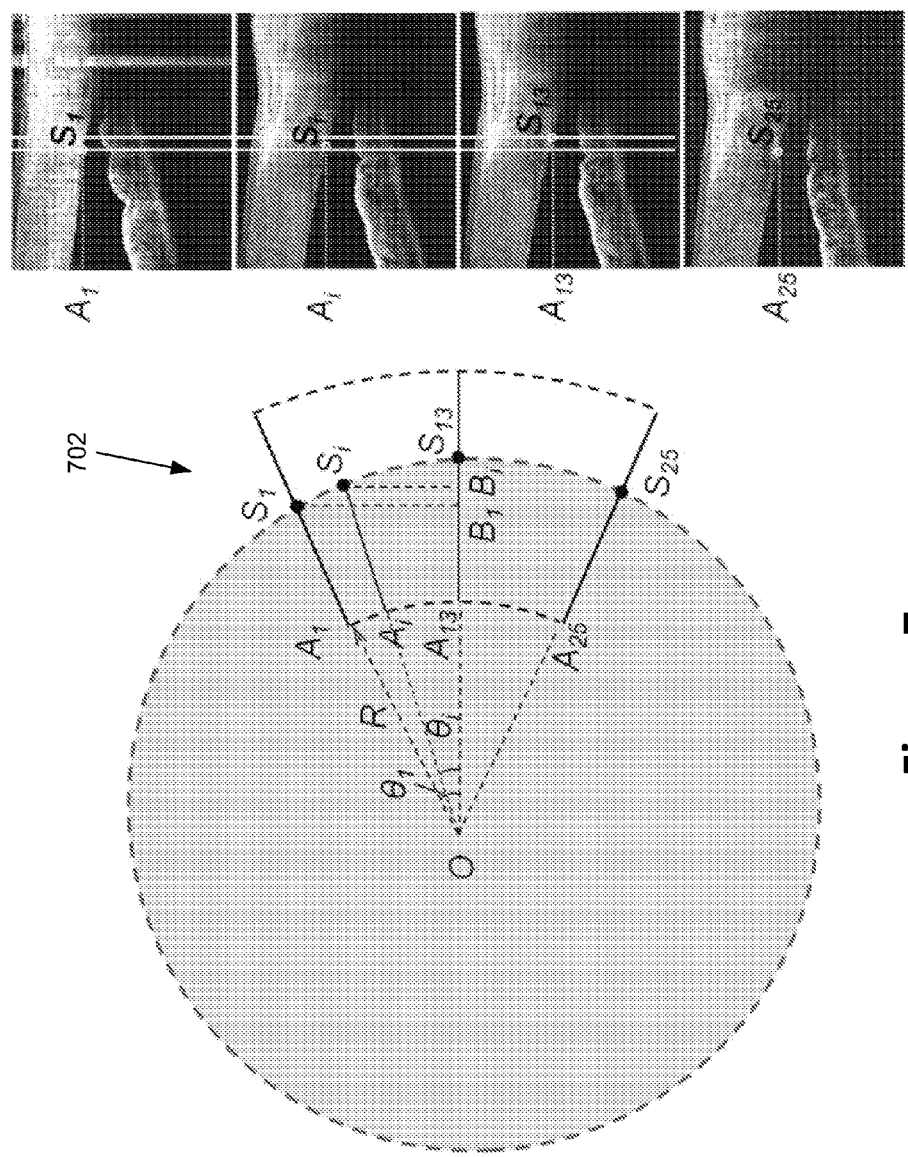
FIG. 7 illustrates the scan pattern illustrated in FIG. 2 converted into a coordinate system and illustrates associated in vivo cross-sectional OCT images, thereby depicting visually the method of locating an anatomical landmark in key frames and intermediate frames within the method shown in FIG. 6.

At 616, the location of the anatomical landmark (e.g., Schwalbe's line) is then calculated at the intermediate frames (2nd-12th and 14th-24$^{th}$ frames). For easier illustration, the scan pattern 202 of FIG. 2A is shown in a coordinate system 702 in FIG. 7. The intersection of the extended radial scan lines is set as the origin O. The 0° scan line is set as the horizontal axis. The scan pattern is shown here as having an inner radius of $OA_i=R=4$ mm, where i=1, 2, . . . , 24, 25. Si is used herewith to denote the Schwalbe's line location in the ith frame. Each radial line scan is arranged evenly 2° apart. An approximation may be made that Bi, which is the projection of Si on the horizontal axis, is evenly spaced between 2 key frames: B1B2=B2B3= . . . =B12B13, and B13B14=B14B15= . . . =B24B25.

Then the transverse location of Schwalbe's line in each frame AiSi can be calculated by triangulation (see Equation 1 below).

$$A_i S_i = \begin{cases} \frac{1}{\cos\theta_i}\left(OB_1 + \frac{(i-1)}{12}(OB_{13} - OB_1)\right) - OA_i, & \text{for } i = 2, \ldots, 12 \\ \frac{1}{\cos\theta_i}\left(OB_{12} + \frac{(i-13)}{12}(OB_{25} - OB_{13})\right) - OA_1, & \text{for } i = 14..24 \end{cases} \quad \text{(Equation 1)}$$

Where $\theta_i = |13 - i| \times 2$; $OB_1 = (R + A_1 S_1)\cos\theta_1$;

$OB_{13} = (R + A_{13}S_{13})$; $OB_{25} = (R + A_{25}S_{25})\cos\theta_{25}$; $OA_i = R$.

$A_1 S_1, A_{13}S_{13}, A_{25}S_{25}$ equaled to the transverse locations of

Schwalbe's line in key frames as obtained in section 2.1.

Next, the transverse location of Schwalbe's line in each frame AiSi can be used to locate Schwalbe's line on the posterior corneal boundary which can be identified in each intermediate frame as noted above in the pre-processing of the 3D angle images description. Similarly, other anatomical landmarks such as scleral spur or angle recess may be detected by manual or automatic methods in key frames and then calculated in intermediate frames.

Generate Synthetic B-Scan and Quantitative 3D Angle Assessment

Figure 8:
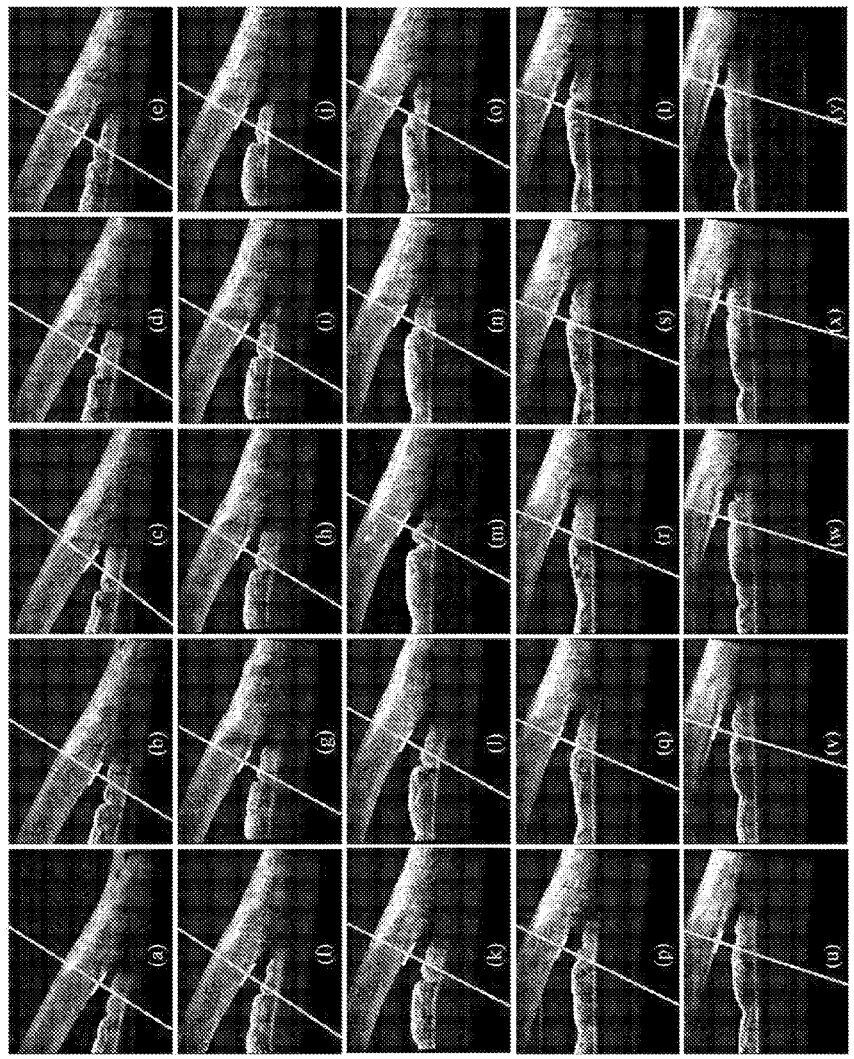
FIG. 8 illustrates resampling of 3D angle scan to generate synthetic B-scan by depicting in vivo cross-sectional OCT 2D image frames of the 3D image volume with lines depicting where pixels are extracted, thereby depicting visually the method of generating synthetic B-scan within the method shown in FIG. 6.
Figure 9:
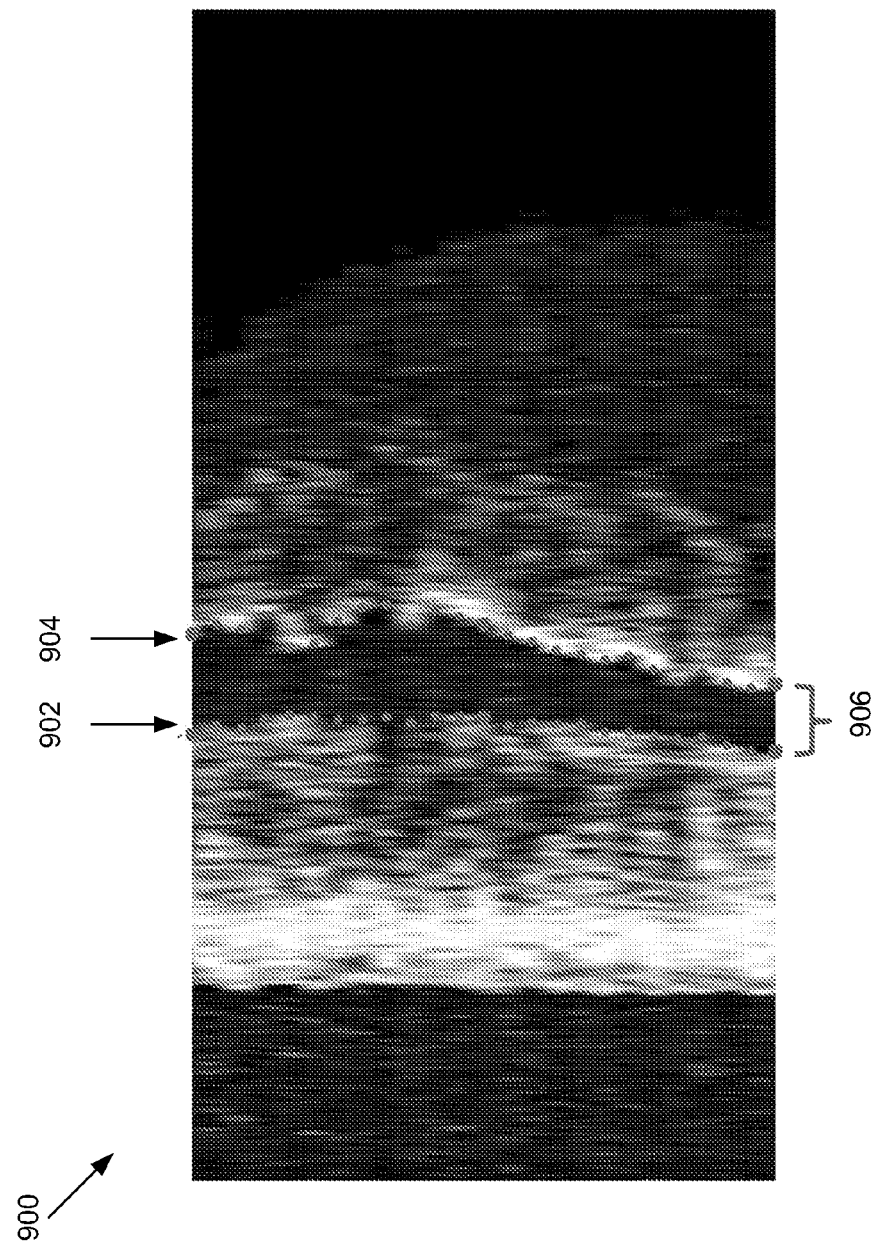
FIG. 9 illustrates a synthetic B-scan of the angle opening distance generated from the extracted pixels of the in-vivo images shown in FIG. 8, and according to the techniques described herein.

At block 618 of method 600, a synthetic B-scan may be generated from respective columns of pixels of each 2D image frame (e.g., line scan) of the 3D scan pattern, with each column of pixels being perpendicular to the posterior corneal surface of the 2D image frame. For example, FIG. 8 illustrates the 2D image frame 802 at each of the 25 frame locations of the 3D scan pattern. A column of pixels 804 perpendicular to the posterior corneal surface may be extracted from each 2D image frame, as represented by the diagonal lines marked in FIG. 8. The extracted pixel columns 804 may then be resampled to the same number of pixels and lined up to generate a synthetic B-scan 900, as shown in FIG. 9. The dark space between Schwalbe's line 902 and the anterior iris 904 may represent the angle opening at Schwalbe's line. Accordingly, the synthetic B-scan 900 may provide a qualitative view of the angle opening variation of the 3D angle area.

Moreover, quantitative measurement of the AOD-SL 906 of the 3D angle area may be obtained from the synthetic B-scan 900. The Schwalbe's line locations 902 may be recorded when obtained according to the methods described above. At block 620 of the method 600, the anterior iris boundary 904 may be identified, e.g., as the first strong peak posterior to Schwalbe's line in the gradient image calculated from the synthetic B-scan. The distance between Schwalbe's line 902 and the anterior iris 904 may represent the AOD-SL 906. At block 622 of method 600, the AOD-SL of the 3D angle area may be calculated.

In various embodiments, the mean, standard deviation (SD), minimum and maximum values of the AOD-SL measurements of the 3D angle may be obtained. The example presented in FIGS. 8 and 9 had an average AOD-SL of 225.6±47.1 μm (mean±SD) with a range of [132.2, 289.7 μm]. At block 624, the method 600 may include outputting the processed 3D angle image, synthetic B-scan, and AOD distribution.

Other Quantitative 3D Angle Measurements

Modified AOD Measurements

Figure 10:
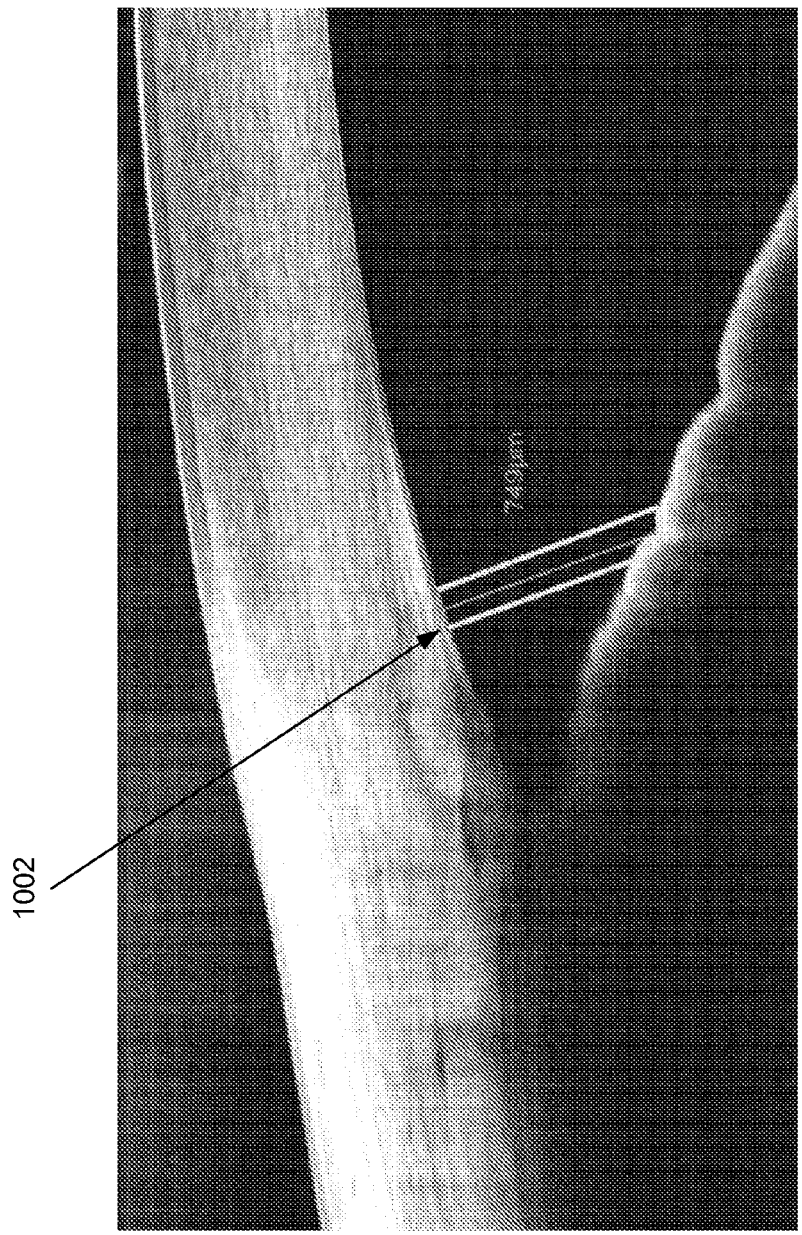
FIG. 10 illustrates an in vivo OCT image showing a modified AOD measurement in accordance with various embodiments.

The AOD measurements obtained can be influenced by iris contour and shape, such as the folds of the anterior iris surface resulting from the changes in the iris as it dilates. The AOD measurement can be larger than it should be if the measurement reaches the fold of the anterior iris surface, as shown in FIG. 10. Modified AOD measurements may solve this problem by averaging the AOD measurements obtained in a small area near the anatomical landmark (e.g., area 1002 shown in FIG. 10).

Modified AOD measurements of the 3D angle scan pattern may be calculated with small modifications to the techniques described above. The mean, SD, minimum and maximum values of the modified AOD measurements of the 3D angle may be obtained from the cross-sectional frames of the 3D scan pattern.

Angle Recess Volume

Figure 11A:
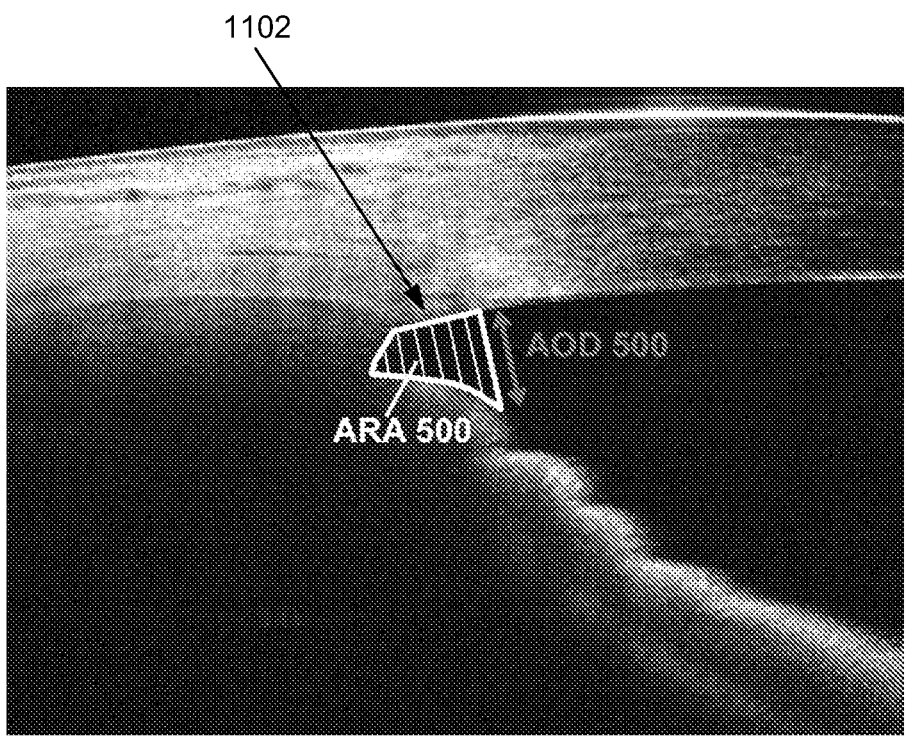
FIG. 11A illustrates an in vivo OCT image showing an angle recess area measurement in accordance with various embodiments.

As shown in FIG. 11A, the angle recess area (ARA) at 500 μm (or 750 μm) may be described as the triangular area 1102 formed by the AOD-SS 500 (or AOD-SS 750), the iris surface, the inner corneoscleral wall, and the angle recess. This is further described in Ishikawa H, Liebmann J, Ritch R., "Quantitative assessment of the anterior segment using ultrasound biomicroscopy," Curr Opin Ophthalmol 2000; 11(2):133-9, which is hereby incorporated by reference.

Figure 11B:
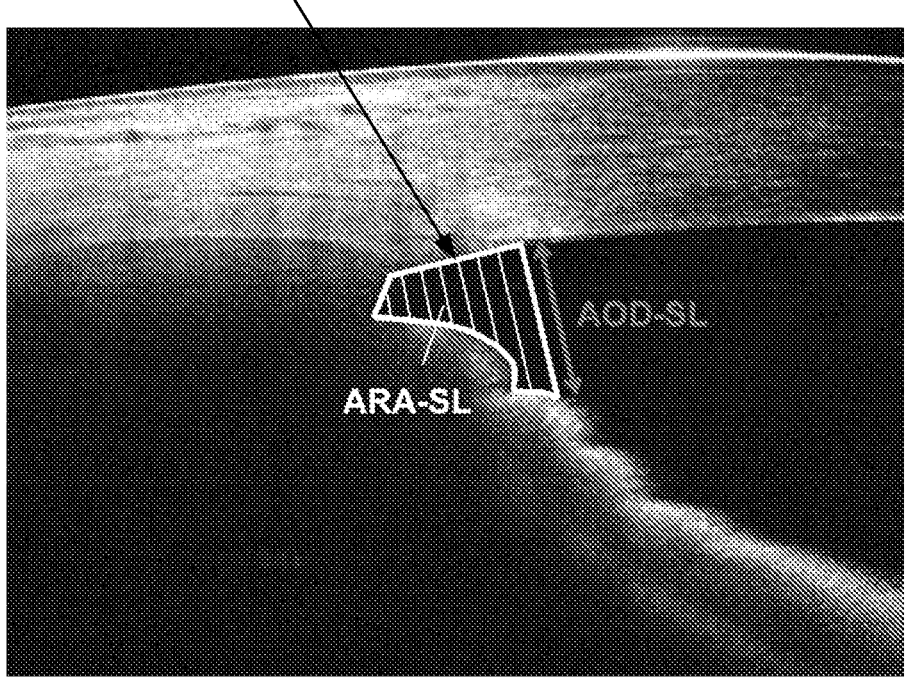
FIG. 11B illustrates an in vivo OCT image showing another angle recess area measurement in accordance with various embodiments.

Alternatively, as shown in FIG. 11B, the ARA 1104 may be defined based on other anatomical landmarks such as Schwalbe's line (e.g., the ARA-SL). The mean, SD, minimum and maximum values of the ARA measurements of the 3D angle scan may be obtained.

Moreover, angle recess volume (ARV) may be calculated by integrating the ARA measurements over the 3D angle scan volume. Various ARA definitions (such as ARA 500, ARA 750, or ARA-SL, etc.) may be used for the ARV calculation.

Trabeculo-Iris Space Volume

Figure 12A:
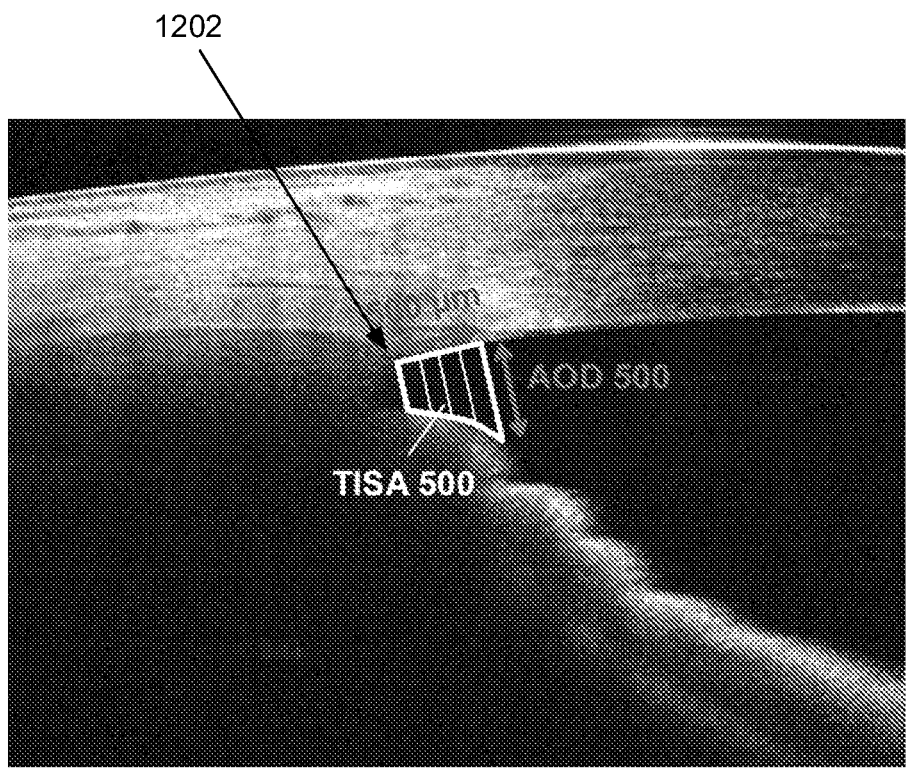
FIG. 12A illustrates an in vivo OCT image of showing a trabeculo-iris space area measurement in accordance with various embodiments.

As shown in FIG. 12A, the trabeculo-iris space area (TISA) at 500 μm (or 750 μm) may be defined as the trapezoidal area 1202 with boundaries of AOD-SS 500 (or AOD-SS 750), a line drawn from the sclera spur perpendicular to the plane of the inner scleral wall to the opposing iris, the inner corneoscleral wall, and the iris surface. This definition of the TISA-SS 500 or TISA-SS 750 is further discussed in Radhakrishnan S, Goldsmith J, Huang D, et al, "Comparison of optical coherence tomography and ultrasound biomicroscopy for detection of narrow anterior chamber angles," Archives of Ophthalmology 2005; 123(8):1053-9, which is hereby incorporated by reference.

Figure 12B:
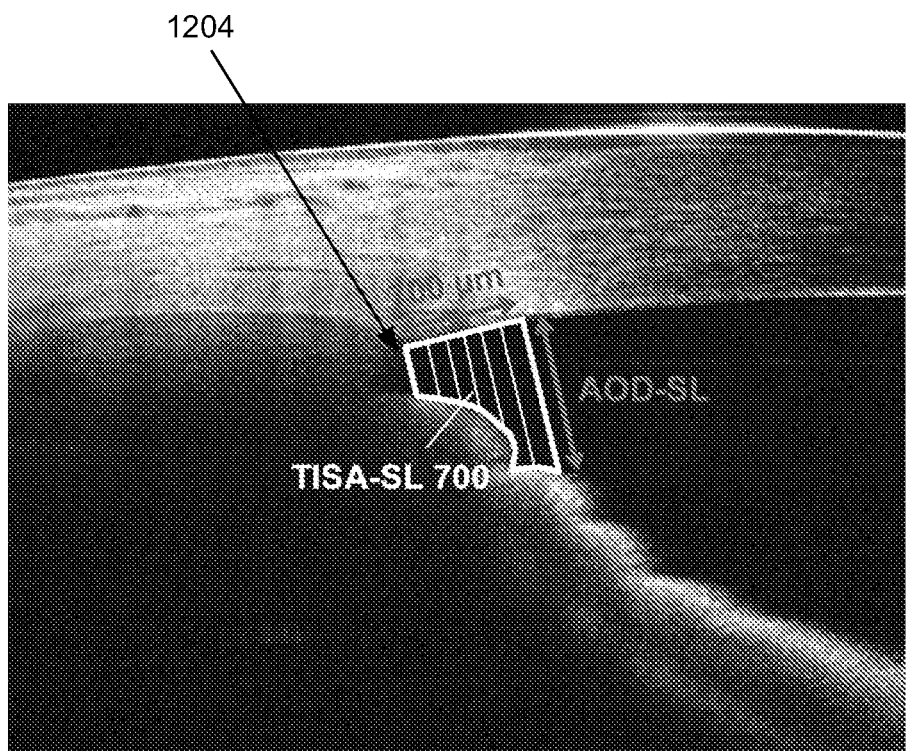
FIG. 12B illustrates an in vivo OCT image showing another trabeculo-iris space area measurement in accordance with various embodiments.

Alternatively, the TISA may be defined based on the posterior length of the trabecular meshwork (TISA-SL), or a fixed distance from the Schwalbe's line (e.g., such as 700 μm based on the average length of the trabecular meshwork, TISA-SL 700, as described in Qin B, Francis B, Li Y, et al, "Anterior chamber angle measurements using Schwalbe's line with high resolution Fourier-domain optical coherence tomography," J of Glaucoma in press, which is hereby incorporated by reference). The TISA-SL is shown, for example, by the area 1204 in FIG. 12B. The mean, SD, minimum and maximum values of the TISA measurements of the 3D angle scan may be obtained.

Trabeculo-iris space volume (TISV) may be calculated by integrating TISA over the 3D angle scan volume. Various TISA definitions (such as TISA 500, TISA 750, TISA-SL, or TISA-SL 700, etc.) may used in the TISV calculation.

Schlemm's Canal Area

Figure 13:
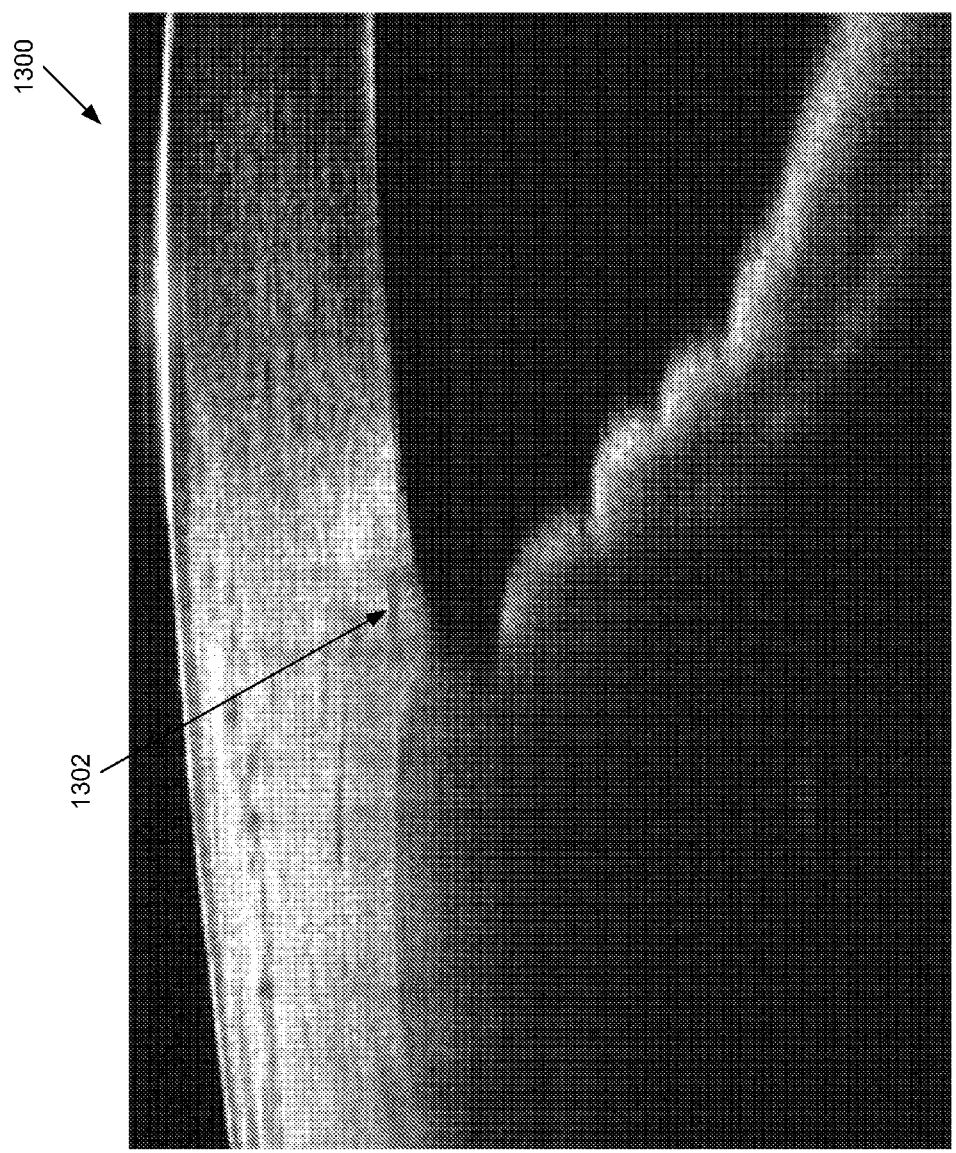
FIG. 13 illustrates an in vivo OCT image showing a Schlemm's canal area measurement in accordance with various embodiments.

In various embodiments, Schlemm's canal area may be measured in the cross-sectional OCT frames (e.g., line scans). For example, FIG. 13 shows a cross-sectional OCT frame 1300 with Schlemm's canal area marked by outline 1302. Average Schlemm's canal area may be calculated by averaging the Schlemm's canal area of the cross-sectional OCT frames in the 3D angle scan volume.

As described above and herewith, the technology disclosed enables the precise 3D angle measurement from the major, pertinent landmarks in the eye. In doing so, the technology enables a more reliable, quantifiable angle measurement test that is both non-invasive and non-contact in nature. Broad patient population can be suited well for OCT Angle Measurement testing including individuals that require angle measurement tests in regular eye exams in substitution of gonioscopy and those individuals that require treatment monitoring, such as patients with angle closure glaucoma patients or patients that have undergone glaucoma surgery.

Very high speed OCT systems with image acquisition rates of multi-million axial scans have been demonstrated. With such high speed, the entire anterior eye segment (e.g., a 360 degree region of the eye) may be imaged in a short time period.

Figure 14:
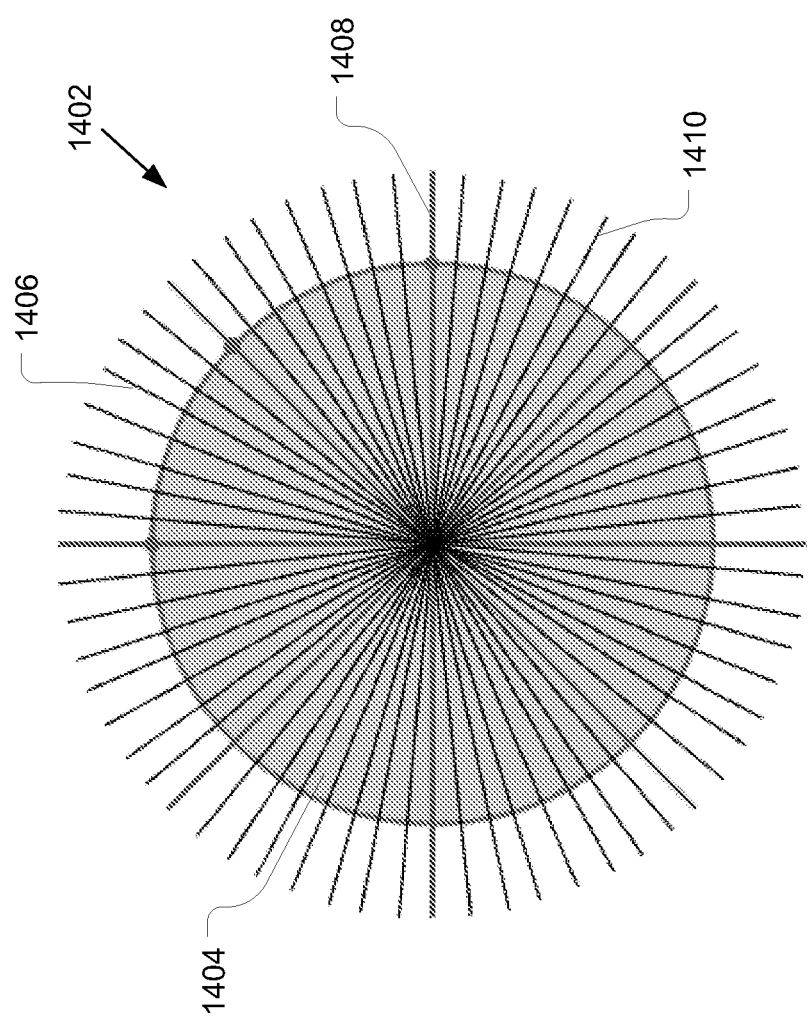
FIG. 14 schematically illustrates a 3D radial scan pattern including radial scans covering a 360 degree region of the eye to image an entire anterior eye segment in accordance with various embodiments.

Further disclosed herein is a method of producing quantified 360 degree 3D angle measurements with no or very limited human input. For example, FIG. 14 illustrates a 3D radial scan pattern 1402 that covers a 360 degree region of an eye 1404. Thus, the radial scan pattern 1402 may also be referred to as a cylindrical scan pattern. The radial scan pattern 1402 includes a plurality of radial line scans 1406 oriented at an angle from one another and oriented in line with a common center point 1405. The radial line scans 1406 are acquired at an even angular distance around a 360 degree region (e.g., 360 degrees around the common center point) of the eye 1404. The radial line scans 1406 each include a plurality of axial scans.

In various embodiments, key frame locations 1408 may be designated in the radial scan pattern 1402. The key frame locations 1408 may be spaced evenly around the radial scan pattern 1402. One or more anatomical landmarks, such as Schwalbe's line, scleral spur, and/or angle recess, may be detected in key-radial locations manually or using computer software. Then, the location of these anatomical landmarks may be calculated in intermediate radial frames 1410 (e.g., using a method similar to that described in the discussion of FIGS. 6 and 7). One or more 3D angle measurements may be calculated on entire 360 degree meridians using the methods described herein. Moreover, radial scans at the key-radial locations may be repeated and averaged to facilitate automatic anatomic landmark detection.

Figure 15A:
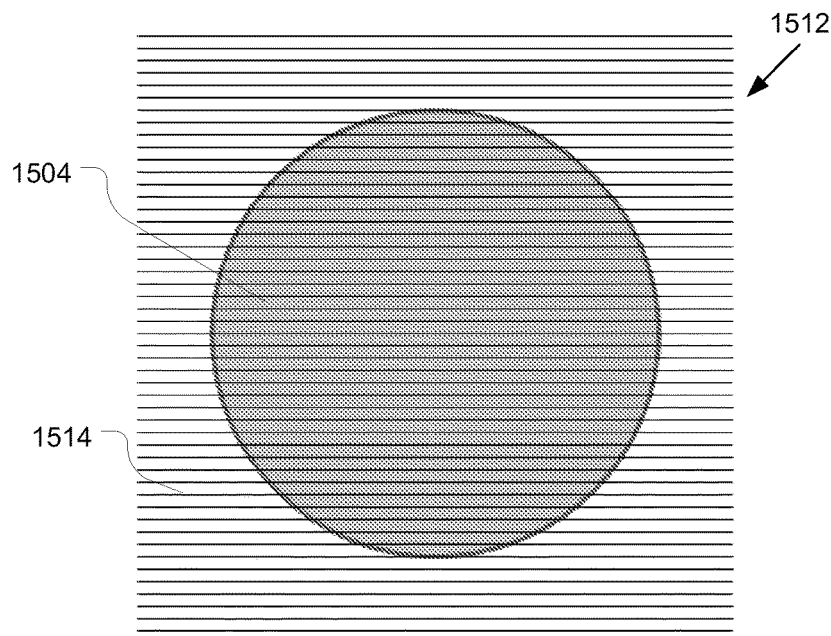
FIG. 15A schematically illustrates a 3D volumetric scan of parallel raster scans covering an entire anterior eye segment in accordance with various embodiments.
Figure 15B:
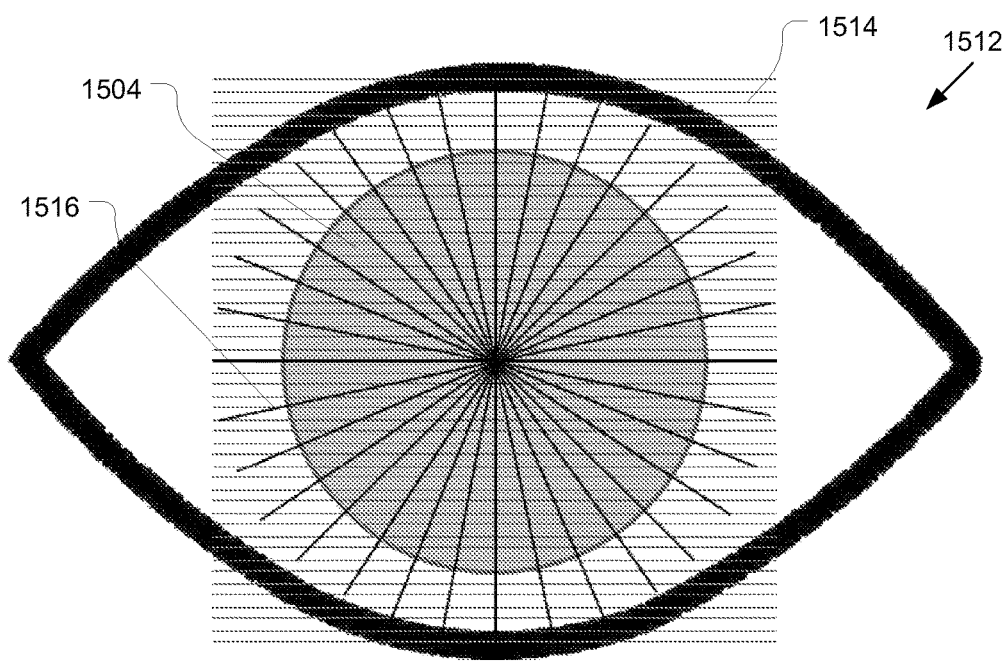
FIG. 15B schematically illustrates how a 3D volumetric scan is resampled to form a cylindrical radial scan pattern in accordance with various embodiments.

Alternatively, as shown in FIG. 15A, raster volumetric scan 1512, including a plurality of parallel line scans 1514, may be used to image the entire anterior eye segment of an eye 1504. The volumetric scan 1512 may be resampled to obtain a radial scan pattern 1516, as shown in FIG. 15B, for quantitative 360 degree 3D angle measurements. In some embodiments, multiple volumetric scans 1512 may be obtained for scan registration and averaging.

The disclosure set forth above encompasses multiple distinct embodiments. While each of these embodiments have been disclosed in its preferred form, the specific embodiments as disclosed and illustrated herein are not to be considered in a limiting sense as numerous variations are possible. The subject matter of the present disclosure includes all novel and non-obvious combinations and subcombinations of the various elements, features, functions and/or properties disclosed herein. Similarly, where any claim recites "a" or "a first" element or the equivalent thereof, such claim should be understood to include incorporation of one or more such elements, neither requiring nor excluding two or more such elements.

What is claimed is:

1. A method of in vivo imaging of an eye, the method comprising:
   receiving a 3-D angle image of an eye comprising a set of line scans acquired at one or more locations;
   locating anterior and posterior corneal boundaries in the 3-D angle image;
   correcting an image distortion resulting from refraction in the 3-D angle image; and
   calculating anatomical landmark locations using the 3-D angle image, wherein the anatomical landmark locations include one or more of Schwalbe's line, scleral spur, angle recess, and/or any location dependent on the anatomical landmark location.

2. The method of claim 1, wherein calculating the anatomical landmark locations further comprises calculating the anatomical landmark locations at one or more intermediate frame locations.

3. The method of claim 2, wherein calculating the anatomical landmark locations further comprises calculating the anatomical landmark locations identified using manual or computerized methods in two dimensional images acquired at one or more key frame locations.

4. The method of claim 2, wherein calculating the anatomical landmark locations at the one or more intermediate frame locations further comprises using one or more triangulation equations.

5. The method of claim 1, wherein the location is 500 microns from the scleral spur.

6. The method of claim 1, further comprising generating a synthetic B-scan.

7. The method of claim 1, further comprising identifying an anterior iris surface in the synthetic B-scan.

8. The method of claim 1, wherein the set of line scans comprises line scans acquired at one or more key frame locations.

9. The method of claim 8, further comprising registering and averaging the line scans acquired at the one or more key frame locations.

10. A method for in vivo imaging of an eye, the method comprising:
    taking a plurality of optical coherence tomography (OCT) line scans of an eye to obtain a 3-dimensional (3D) fan-shaped scan pattern, the individual line scans including a plurality of axial scans, wherein taking the plurality of line scans includes taking a plurality of radial line scans, with adjacent radial line scans oriented at an angle from one another, to form the fan-shaped pattern; and
    obtaining a three-dimensional image of an anterior chamber angle of the eye from the fan-shaped pattern.

11. The method of claim 10, wherein the taking the plurality of line scans includes:
    taking a plurality of line scans at one or more key frame locations in the radial scan pattern for frame averaging; and
    taking a single line scan at one or more intermediate locations in the radial scan pattern.

12. The method of claim 11, wherein the one or more key frame locations are evenly spaced in the fan-shaped scan pattern.

13. The method of claim 10, wherein the line scans have a length of about 3 millimeters (mm) to about 10 mm, and the angle at which adjacent radial line scans are oriented is about 0.5 to about 5 degrees.

14. The method of claim 10, wherein the plurality of line scans include a plurality of parallel line scans of a volumetric scan, and wherein the fan-shaped scan pattern is obtained by resampling the volumetric scan to form a plurality of radial line scans from the plurality of parallel line scans.

15. The method of claim 10, wherein the fan-shaped scan pattern is a first fan-shaped scan pattern, the three-dimensional image is a first three-dimensional image, and the method further includes:
    taking a plurality of OCT line scans of the eye to obtain a second fan-shaped scan pattern, wherein the second fan-shaped scan pattern has a different orientation with respect to the eye compared with the first fan-shaped scan pattern; and
    obtaining a second three-dimensional image of the anterior chamber angle of the eye from the second fan-shaped scan pattern.

16. The method of claim 10, wherein the fan-shaped scan pattern is a first fan-shaped scan pattern, and wherein the method further includes:
    obtaining a second fan-shaped scan pattern at a same location of the eye as the first fan-shaped scan pattern; and
    averaging the first and second fan-shaped scan patterns to facilitate identification of one or more anatomical landmarks.

17. The method of claim 10, further comprising:
    averaging a plurality of radial line scans of the radial scan pattern at one or more key frame locations of the fan-shaped scan pattern; and
    identifying one or more anatomical landmarks of the eye from the plurality of line scans at the one or more key frame locations.

18. The method of claim 17, wherein the anatomical landmark is Schwalbe's line, a scleral spur, or an angle recess of the eye.

19. The method of claim 17, further comprising calculating a location of the one or more anatomical landmarks in intermediate line scans based on the identification of the one or more anatomical landmarks at the one or more key frame locations.

20. The method of claim 10, further comprising:
    extracting a column of pixels from individual frames of the fan-shaped scan pattern at a plurality of frame locations of the fan-shaped scan pattern, the columns of pixels having a common orientation with respect to one or more anatomical landmarks; and aligning the extracted columns of pixels to form a synthetic B-scan.

21. The method of claim 20, wherein the columns of pixels are perpendicular to a posterior corneal surface of the eye.

22. The method of claim 21, further comprising measuring an angle opening distance (AOD) of the eye from the synthetic B-scan.

23. The method of claim 22, wherein the AOD is measured as a distance from the one or more anatomical landmarks to an anterior iris boundary of the eye.

24. The method of claim 22, further comprising calculating a mean, standard deviation, minimum value, or maximum value of the AOD from the synthetic B-scan.

25. The method of claim 22, wherein the synthetic B-scan is a first synthetic B-scan, and the method further comprises:
obtaining a plurality of synthetic B-scans including the first synthetic B-scan;
taking AOD measurements from the plurality of synthetic B-scans; and
averaging the AOD measurements from the plurality of synthetic B-scans to obtain a modified AOD measurement.

26. The method of claim 10, further comprising:
measuring an area of a region of the eye in a plurality of frames of the radial scan pattern, the region defined by one or more anatomical landmarks; and
calculating a volume of the region based on the measured areas.

27. The method of claim 26, wherein the area is an angle recess area, and the volume is an angle recess volume.

28. The method of claim 26, wherein the area is a trabeculo-iris space area, and the volume is a trabeculo-iris space volume.

29. The method of claim 10, further comprising:
measuring Schlemm's canal area in a plurality of frames of the radial scan pattern; and
obtaining a mean, standard deviation, minimum value, or maximum value of Schlemm's canal area from the measured Schlemm's canal areas.

30. One or more non-transitory, computer-readable media having instructions, stored thereon, that, when executed, cause a computing system to:
acquire a 3-dimensional (3D) optical coherence tomography (OCT) radial scan pattern of an eye, the fan-shaped scan pattern including a first number of radial line scans at a plurality of key frame locations and a second number of radial line scans at a plurality of intermediate frame locations, the first number being larger than the second number, and the individual radial line scans including a plurality of axial scans;
identify a location of one or more anatomical landmarks of the eye at the key frame locations from the radial line scans at the key frame locations; and
calculate a location of the one or more anatomical landmarks at the intermediate frame locations based on the identified locations of the one or more anatomical landmarks at the key frame locations.

31. The one or more computer-readable media of claim 30, wherein the anatomical landmark is Schwalbe's line, a scleral spur, or an angle recess of the eye.

32. One or more non-transitory, computer-readable media having instructions, stored thereon, that, when executed, cause a computing system to:
acquire a 3-dimensional (3D) optical coherence tomography (OCT) fan-shaped scan pattern of an eye, the fan-shaped scan pattern including fan-shaped line scans at a plurality of frame locations oriented at an angle from one another, and the individual radial line scans including a plurality of axial scans;
extract a column of pixels from the fan-shaped line scans at the plurality of frame locations of the fan-shaped scan pattern, the columns of pixels having a common orientation with respect to one or more anatomical landmarks of the eye; and
align the extracted columns of pixels to form a synthetic B-scan.

33. The one or more computer-readable media of claim 32, wherein the columns of pixels are perpendicular to a posterior corneal surface of the eye.

34. The one or more computer-readable media of claim 33, wherein the instructions, when executed, further cause the computing system to measure an angle opening distance (AOD) of the eye from the synthetic B-scan.

35. The one or more computer-readable media of claim 34, wherein the AOD is measured as a distance from one or more anatomical landmarks to an anterior iris boundary of the eye.

36. The one or more computer-readable media of claim 34, wherein the synthetic B-scan is a first synthetic B-scan, and the instructions, when executed, further cause the computing system to:
obtain a plurality of synthetic B-scans including the first synthetic B-scan;
take AOD measurements from the plurality of synthetic B-scans; and
average the AOD measurements from the plurality of synthetic B-scans to obtain a modified AOD measurement.

* * * * *

UNITED STATES PATENT AND TRADEMARK OFFICE
CERTIFICATE OF CORRECTION

PATENT NO. : 9,579,016 B2
APPLICATION NO. : 14/407668
DATED : February 28, 2017
INVENTOR(S) : David Huang et al.

Page 1 of 1

It is certified that error appears in the above-identified patent and that said Letters Patent is hereby corrected as shown below:

In the Specification

At Column 1, Lines 18-21, under the heading ACKNOWLEDGEMENT OF GOVERNMENT SUPPORT, please delete the following:
"This invention was made with government support under grant numbers R01-EY018184 awarded by the National Institutes of Health. The government has certain rights in the technology."

And replace it with the following:
-- This invention was made with government support under EY018184 awarded by the National Institutes of Health. The government has certain rights in the invention. --

Signed and Sealed this
Twenty-second Day of October, 2019

Andrei Iancu
*Director of the United States Patent and Trademark Office*